(12) United States Patent
Lee

(10) Patent No.: US 9,063,072 B1
(45) Date of Patent: Jun. 23, 2015

(54) BIREFRINGENCE CORRECTION FOR IMAGING ELLIPSOMETRIC BIOASSAY SYSTEM AND METHOD

(75) Inventor: Claudia Yi-Chen Lee, Altadena, CA (US)

(73) Assignee: Maven Technologies, LLC, Monrovia, CA (US)

( * ) Notice: Subject to any disclaimer, the term of this patent is extended or adjusted under 35 U.S.C. 154(b) by 398 days.

(21) Appl. No.: 13/494,866

(22) Filed: Jun. 12, 2012

(51) Int. Cl.
| | | |
|---|---|---|
| *G01J 4/00* | (2006.01) | |
| *G01N 21/55* | (2014.01) | |
| *G01N 21/27* | (2006.01) | |
| *G01N 21/552* | (2014.01) | |
| *G01N 21/23* | (2006.01) | |
| *G01J 4/04* | (2006.01) | |
| *G01N 21/19* | (2006.01) | |
| *G01N 21/64* | (2006.01) | |
| *G01N 21/21* | (2006.01) | |

(52) U.S. Cl.
CPC ........ *G01N 21/274* (2013.01); *G01N 2021/212* (2013.01); *G01N 21/553* (2013.01); *G01N 21/23* (2013.01); *G01J 4/04* (2013.01); *G01N 21/19* (2013.01); *G01N 21/648* (2013.01)

(58) Field of Classification Search
CPC ............... G01J 4/00; G01J 4/04; G01J 3/447; G01N 21/211; G01N 21/553; G01N 21/648; G01N 21/21; G01N 21/253; G01N 21/274; G01N 2021/212; G01N 2021/213; G01N 21/23; G01N 21/19
USPC .......................................... 356/356, 369, 445
See application file for complete search history.

(56) References Cited

U.S. PATENT DOCUMENTS

| | | | |
|---|---|---|---|
| 4,737,005 A | 4/1988 | Burns | |
| 6,594,011 B1 | 7/2003 | Kempen | |
| 6,798,511 B1* | 9/2004 | Zhan et al. ..................... 356/369 |
| 6,833,920 B2 | 12/2004 | Rassman | |
| 6,859,280 B2 | 2/2005 | Kempen | |
| 7,023,547 B2 | 4/2006 | Venkatasubbarao | |
| 7,126,688 B2 | 10/2006 | Rassman | |
| 7,369,235 B1* | 5/2008 | Janik et al. ..................... 356/369 |
| 7,518,724 B2 | 4/2009 | Rassman | |
| 7,799,558 B1 | 9/2010 | Dultz | |
| 7,807,105 B2 | 10/2010 | Goshoo | |
| 7,863,037 B1 | 1/2011 | Dultz | |
| 7,867,783 B2 | 1/2011 | Dultz | |
| 8,119,391 B2 | 2/2012 | Kim | |
| 2004/0130723 A1* | 7/2004 | Yager et al. .................... 356/445 |
| 2005/0012041 A1* | 1/2005 | Garcia-Caurel et al. . 250/339.01 |
| 2005/0264813 A1* | 12/2005 | Giakos .......................... 356/369 |
| 2007/0058166 A1* | 3/2007 | Rassman et al. .............. 356/369 |

(Continued)

OTHER PUBLICATIONS

Wikipedia, Biochip, http://en.wikipedia.org/wiki/Biochip.

*Primary Examiner* — Tarifur Chowdhury
*Assistant Examiner* — Sunghee Y Gray
(74) *Attorney, Agent, or Firm* — Lawrence S. Cohen

(57) ABSTRACT

A system, apparatus and method for analysis of a specimen using ellipsometric analysis. Polarization distortions caused by the propagation of polarized light within a substrate upon which a specimen is located are reduced by directing light at selected polarizations at the substrate alone and the specimen on the substrate. Image data is collected for each of the selected polarizations and processed to remove errors due to birefringence. Fourier transform processing is used to obtain polarization phase data for correcting polarization caused by any birefringence in the substrate, and optionally amplitude data.

10 Claims, 10 Drawing Sheets

(56) References Cited

U.S. PATENT DOCUMENTS

| | | |
|---|---|---|
| 2009/0141376 A1* | 6/2009 | Smith et al. .................. 359/833 |
| 2009/0296246 A1* | 12/2009 | Yamada et al. ............... 359/885 |
| 2010/0172150 A1 | 7/2010 | Saito |
| 2011/0216320 A1* | 9/2011 | Cho et al. ..................... 356/369 |
| 2011/0299270 A1 | 12/2011 | Kojima |
| 2012/0038987 A1 | 2/2012 | Iizuka |

\* cited by examiner

BIREFRINGENCE CORRECTION FOR IMAGING ELLIPSOMETRIC BIOASSAY SYSTEM AND METHOD

STATEMENT REGARDING FEDERALLY SPONSORED RESEARCH OR DEVELOPMENT

The U.S. Government has certain rights in this invention pursuant to Grant No. 1RC3AI089277-01 awarded by Department of Health and Human Services, National Institutes of Health, National Institute of Allergy and Infectious Diseases.

BACKGROUND

1. Field

This disclosure relates to specimen analysis through the use of ellipsometry. More particularly, the present disclosure describes improvements in ellipsometric performance during specimen analysis by reducing the impact of birefringence.

2. Description of Related Art

There are numerous categories of procedures under the general heading of bioassay. Here is a list that is at least exemplary if not exhaustive of the type of bioassays in which the technology known as imaging ellipsometry or sometimes evanescent field imaging is or can be applied:

1. Label free DNA hybridization assay. Microarray of single strand DNA can be placed on the surface of the substrate. The binding of the corresponding strand from a sample under study can be detected. The implementation is often used for DNA sequencing and called a DNA chip.

2. Label free protein assay. Microarray of proteins can be placed on the surface of the substrate. The binding of the corresponding molecular target can be detected. If the binding molecule is disease related, often peptides, protein produced by the disease, by the host, the protein assay can be used for diagnostic purposes.

3. Small molecule discovery assay. A panel of possible biomarker drug candidates can be placed on the substrate. A sample containing the target, often a protein that would trigger a cascade reaction, would be applied and the selective binding can be observed.

4. Label free micro-organism capturing assay. Molecules, for example, targeting specific micro-organism can be placed on the surface of the substrate. When the solution containing the specific organism, such as cells, parasites and bacteria, is applied, the organism captured at the surface can be detected. A micro-organism capturing assay can be used for capturing, diagnostic or environmental purposes. The molecule placed on the substrate can be protein, lipid, sugar, bio-inert molecules such as PEG, or a composition of these molecules.

5. Cell-based assay. Cells can be placed on the surface of the substrate. Stimulation is introduced to the cells, and the reaction is measured through the reaction footprint of the cells. The dosage and efficacy of the stimulation can be quantified through the reaction of the cells. The typical cell-based assay includes proliferation assay, wound healing assay, toxicity assay. Also the indirect target of the stimulation can be studied through performing the cell-based assay. For example, genetically engineered cells which over or under express a targeted protein can have medicated reaction under the reaction of the stimuli.

U.S. Pat. No. 6,859,280 discloses an imaging ellipsometry system which employs a transparent substrate and directs polarized light at the upper surface of the substrate in a manner to produce total internal reflection (TIR) and an evanescent field at the upper surface of the substrate. The system disclosed in U.S. Pat. No. 6,859,280 is designed to sense chemical reactions occurring in an evanescent field at the upper surface of the substrate by sensing intensity changes at locations of the surface which correspond to pixel locations in a two-dimensional sensor such as a charge coupled device (CCD) to which reflected light is directed. The chemical reactions occur by immobilizing an array of receptors on the upper surface of the substrate and sensing changes in polarization of the reflected light due to binding events between analytes (ligands) in a sample introduced to the surface and receptors in the array. Alternatively, a drug is introduced to cells cultured at the upper surface of a transparent substrate for analysis as, for example, by a dose response to carbachol, a cholinergic receptor agonist, resulting in changes to the cells' footprint on the substrate surface sensed as localized intensity changes in the reflected light. Cells are naturally spatially distributed. By producing an image, it allows selective analysis of the changes in the polarization state in the cross-section of the reflected beam which are indicative of the substances in the specimen in the location corresponding to a position in the detector. Therefore, the system may be configured to produce an image which represents the change in polarization state within each of the discrete specimen spots or within the footprint of cultured cells. That change can then be output as an image of physical measurement of physical properties such as density or height. The image refers to a set of values correlated to different spatial positions which can be displayed or compared against each other to contrast differences in physical properties at these positions.

Multiwell disposables used to contain specimens for analysis are commonly available. For ellipsometric systems where polarized light is employed in the imaging system, the disposable (slide or well) should be birefringence-free to avoid significant reduction of sensitivity in the detection (imaging) of binding events. Birefringence free disposables are usually made from glass and are too expensive to be used in large segments of the market for ellipsometric systems. Plastic disposables, on the other hand, are sufficiently inexpensive to be useful in virtually every segment of the market. But plastics, although promising, presently exhibit birefringence which reduces the sensitivity of system output signals and thus the usefulness of the systems.

As indicated above, most existing ellipsometry implementations require a high performance optical material as the substrate which does not alter the relative phase of the two polarizations outside the binding surface. The high performance requirement is an obstacle in reducing the cost of performing ellipsometry and is not always achievable in common optical material. Birefringence in material, which is a phenomenon where the speed of light depends on its direction, can contribute to the polarization phase measured and skew the measured result on binding. That is, birefringence in the material on which a specimen is distributed will skew the polarization phase changes of the light transmitted to the sensor. Hence, the measured polarization may not accurately reflect the polarization change arising from biochemical interactions.

Therefore, there exists a need to improve the collection and processing of birefringence-impacted ellipsometry data to allow for lower cost optical material to be used and/or to allow for faster processing of the data.

SUMMARY

The invention disclosed here describes ways of using existing, 2D detector array based, imaging ellipsometry instruments to measure surface refractive index changes due to increase of surface binding or changes in quality of binding on a birefringent substrate. Fourier transformation is used along with polarization modification apparatus to calculate and reduce the impact of birefringence in a specimen-carrying substrate. The combination of Fourier processing and polarization modification allows for ellipsometry to be performed simultaneously at every point of the detector array, resulting in fast, accurate measurements without requiring a birefringence-free substrate.

The invention is based on the recognition that the effects of birefringence in a substrate on ellipsometry measurements on a pattern of specimens on an area of the substrate surface can be obviated by performing Fourier transform calculations on the intensity of cyclically rotating polarized light reflected from the area of the substrate surface and captured by a 2-D detector. Fourier transformation operates to calculate a phase and amplitude for each pixel in the image of the reflected light at each of at least four equally spaced angles in each cycle. Birefringence free ellipsometry measurements of the reflected light at each pixel in the image is obtained by subtracting the measurement taken in the absence of the specimens from the measurement taken with the specimens.

DETAILED DESCRIPTION

The exemplary embodiments according to the present invention described in this disclosure provide for analysis of a specimen using ellipsometric analysis while overcoming performance degradation caused by substrate birefringence.

The term "specimen" or "specimen spot" or "specimen array" is used to describe a substance or group or array of substances present on the reflection surface of a substrate and within the evanescent field caused by single internal reflection in the substrate so as to be measured by processes and apparatus and systems described herein. In some contexts the term specimen may refer to a substrate with chemicals on it. Sometimes the chemicals are referred to as "probes" or "receptors" and the chemical whose presence or quantity is under study is called an "analyte" or "target" which typically will bind with the receptor, the goal being to measure the difference or absence of difference at the location of the receptor so as to determine that a binding event has or has not occurred. Also, in the case of cell reaction, the reaction can be detected and measured. The present invention also allows readings over time so that temporal changes can be observed. It will be apparent that the invention can be implemented for any circumstance where a change at one or more locations is desired to be imaged over a two dimensional area and the imaging showing changes in the amount or quality of substance at imaged locations. In addition to imaging, data results can also be obtained. The term "image" is used in the conventional sense to a display or other access to a viewable image and also, in context, as defining a two-dimensional detection event relating to an array of pixels such as intensity or phase shift.

The content of each of the following US patents is incorporated herein by this reference; U.S. Pat. Nos. 7,981,664; 7,867,783; 7,863,037; 7,799,558; 7,518,724; 7,126,688; 7,023,547; 6,859,280; 6,833,920; and 6,594,011.

Figure 1:
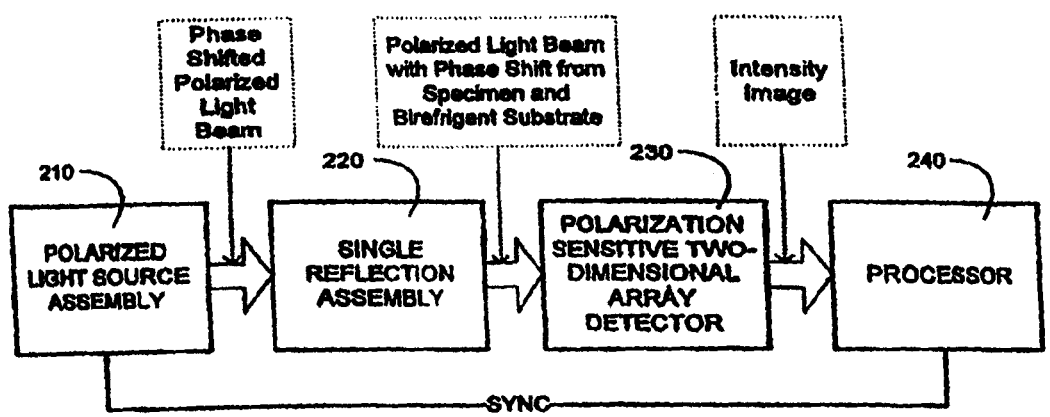
FIG. 1 is a block diagram of a system for ellipsometric analysis where polarization orientation is synchronized to image data capture and birefringence is present.

FIG. 1 shows an imaging ellipsometric measurement system exemplary of the present invention. As shown in FIG. 1, a polarized light assembly 210 generates a beam of polarized light with two perpendicular directions of polarization. That light is directed towards a single reflection assembly 220 configured to hold specimens to be analyzed. The reflection assembly 220 reflects the polarized light beam where the polarization of the reflected polarized light beam is impacted by the substrate through which the light passes and the specimens under analysis. The reflected polarized light beam is directed towards a polarization sensitive two dimensional detector 230 that provides an image for analysis by a processor 240. The processor 240 is synchronized with the polarized light assembly 210 to link the phase of the light produced by the assembly 210 with the image received by the processor 240. See below for a more detailed explanation of FIG. 2.

Figure 2:
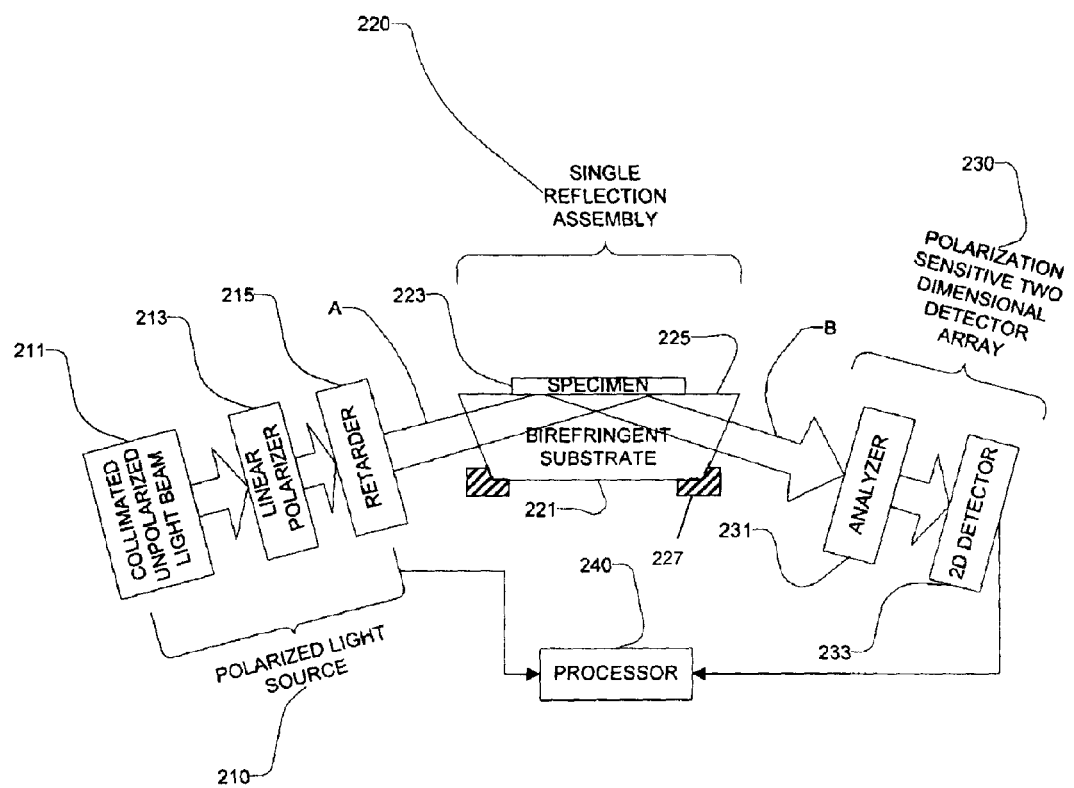
FIG. 2 shows a schematic block diagram of a system for ellipsometric analysis, in which the impact of birefringence is reduced.

In schematic form, FIG. 2 illustrates an embodiment of the invention for ellipsometry measurement as in the block diagram of FIG. 1. The apparatus can be defined as a single internal reflection apparatus having a polarized light source, a detector assembly and a positioning mechanism for placement of a biochip (variously called bioarray, and microarray and other terms) having biological substances for obtaining information about chemical or biological reactions or events on the biochip. A processor is included to process the data obtained. As shown in FIG. 2, the polarized light source 210 may comprise a collimated unpolarized light beam source 211, a linear polarizer 213, and a retarder 215. The linear polarizer 213 produces the linearly polarized light beam from the unpolarized light beam source 211. The retarder 215 then produces a light beam "A" with a selected polarization, preferably a circularly polarized light beam having two perpendicular directions of polarization.

The positioning mechanism comprises supporting and placement structure, schematically shown at 227, for holding the single reflection assembly 220 (the biochip or other device) under examination in the correct position for single internal reflection. Each of the polarized light source, the detector assembly and the positioning portion may be adjustable in order to accomplish the desired optical effects. The positioning portion 227 may be equipped to change the position of a biochip under examination to place different 2 dimensional areas of its surface within the illumination of the light beam A and to effect its reflection B.

The light beam "A" is directed towards the single reflection assembly 220, which has a specimen 223 placed on a reflection surface 225 of a birefringent substrate 221 which is configured as a prism, or equivalent form (see FIGS. 8-10) to direct the polarized light beam for a single internal reflection at the reflection surface 225 whereby an evanescent field is established, the specimen being within the evanescent field. Upon the single reflection at the reflection surface 225, the phase of the light with polarization pointing into the specimen changes relative to the light with polarization pointing parallel to the interface. The objective of the ellipsometric measurement system is to measure this phase change, i.e., polarization change caused by the specimen. However, the birefringent substrate 221 may add to this relative phase shift as a function of the path of light within the substrate 221.

The light beam "B" reflected out of the single reflection assembly 220 is directed towards the detector assembly, defining a polarization sensitive two dimensional detection array 230, which has an analyzer 231 and a two dimensional detector 233. The two dimensional detector 233 is an array of intensity sensors which produces an intensity output at each sensor that is sent to the processor 240. Each of the sensors in the array will be referred to as a pixel in this description. The relative phase shift of the reflected light beam, whether the phase shift results from the specimen, birefringence in the substrate, or both, changes the intensity measured by the polarization sensitive two-dimensional array 230. The processor 240 receives intensity data from the two dimensional detector 233 and is also synchronized with polarization settings of the polarized light source 210. The processor is programmed to produce an image indicating the physical condition at each pixel in the 2D array of specimens. Operation of the processor as programmed is described below.

The polarized light source 210 may be configured to produce light with different polarizations or different polarization orientations with respect to the single reflection assembly 220. Changes to polarization or polarization orientation may be made by rotating the linear polarizer 213, rotating the analyzer 231, or changing the retardation value of the retarder 215 to effect polarization phase of the beam "A". As indicated above, the polarizations obtained by rotating the polarizer and/or retarder and/or changing retardation values are synchronized with the image intensity values received by the processor.

Figure 8:
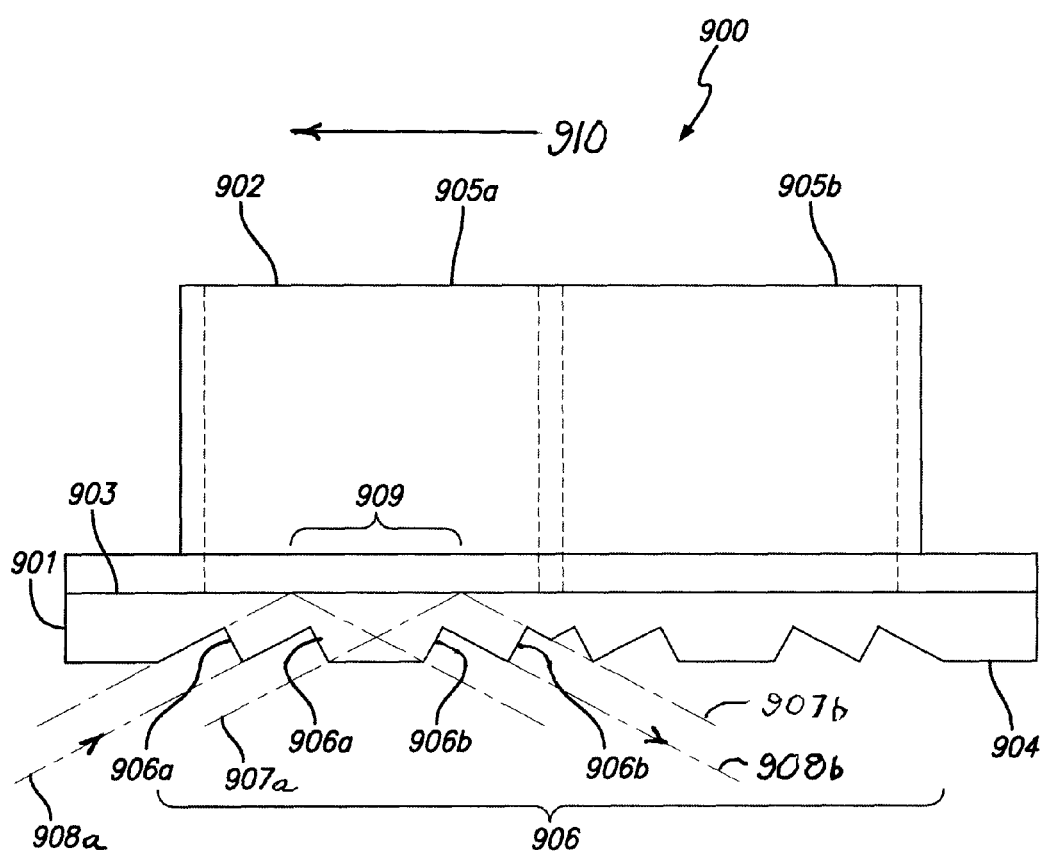
FIG. 8 depicts an end view of a substrate having a single groove for a single light receiving incident prismatic surface and a single light exiting prismatic surface with an evanescent field resulting from the single internal reflection.
Figure 9:
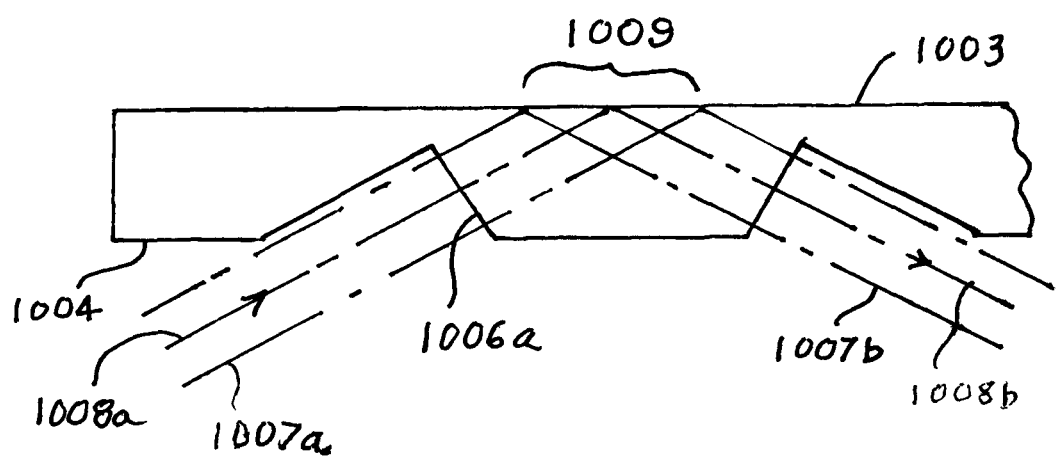
FIG. 9 depicts the assembled slide and multiwell plate of FIGS. 6 and 7 showing the beam of polarized light passing through the slide and reflecting off the surface on which specimens are deposited and including the substrate having a plurality of grooves defining two prismatic light incident surfaces and two prismatic light exiting surface with an evanescent field resulting from the single internal reflection.

In the system shown in FIGS. 1 and 2, low or non-birefringent optical components may be chosen to reduce or eliminate the impact of birefringence on the measured polarization. However, plastic slides are relatively low cost, so replacement of plastic slides with non-birefringent glass slides results in significantly increased costs. Disposable plastic multiwell slides or plastic slides with multiple specimen depressions or simply with arrays of spots are typically used in biological specimen analysis. FIGS. 8-10 depict an exemplary multiwell slide. Such plastic slides allow for the simultaneous analysis of several specimens. It is advantageous to address and reduce or eliminate the birefringence of the plastic slides during ellipsometric analysis.

The present invention addresses the problem of birefringence contaminating ellipsometry measurement of specimens by use of a Fourier transform ellipsometry technique. That technique, is generally described for determining polarization with the exemplary system shown in FIGS. 1 and 2. In summary, the relative phase of the light used to illuminate a substrate is changed to several values (at least four) and intensity measurements made at each point on the imaging array corresponding to a specimen to be analyzed at each of the relative phase values. Intensity measurements are made at each pixel of the imaging array detector. A Fourier transform is performed on the measurements made for each pixel to solve for the phase of light altered by the specimens under analysis. Performance of Fourier Transforms for each point or pixel can then be used to provide a two-dimensional image depicting the polarization at each point or pixel. Note that this Fourier transform ellipsometry requires at least 4 different relative light phases and additional relative light phases may be needed to achieve desired precision in the determined specimen polarizations. The four different relative light phases are equally spaced within an angular cycle of 360° (e.g. 0°, 90°, 180°, 270°), subject to the requirements of Table 1 below. The advantage of Fourier Transform ellipsometry is that light having only at least four different phases is required for measuring polarization phase in the entire array. This technique then is used to measure the error in polarization phase change introduced by the non-birefringence free substrate and also the total polarization phase shift of the substrate and the specimens, and subtracting the results to eliminate that effect caused by the substrate alone.

A non-perfect (i.e., a non-birefringence free) substrate containing no specimen is inserted into a system such as the one depicted in FIGS. 1 and 2. The substrate is then sequentially illuminated with light at (at least) four different phases for each pixel in the two dimensional area at which specimens may be placed. Each point is referred to as a pixel as related to the sensor mechanism used. A Fourier transformation is performed on the data for measurements made for each pixel to solve for the phase of light altered by the non-perfect material. Specimens are then added to the substrate and the relative phase changes of the light and intensity measurements are repeated. A Fourier transformation is then performed on the measurements made for each pixel of the substrate-specimen combination to solve for the phase of light at each pixel. The calculated polarization phase change contributed by the substrate can then be subtracted from the calculated polarization phase change of the substrate-specimen combination to obtain the phase change of the specimens alone at each or pixel. The phases acquired by Fourier transform ellipsometry add on top of each linearly, so simple subtraction provides the phase change of the specimen alone.

There are several methods to achieve this Fourier transform ellipsometry. These methods include: 1) use of a rotating polarizer; 2) changing the retardation value; 3) use of a rotating retarder; and 4) use of a rotating analyzer. Methods 1 and 2 are mathematically equivalent. Method 3 and 4 provide inferior results when compared to the first two methods. In the system depicted in FIGS. 1 and 2, methods 1, 2, or 3 may be implemented within the polarized light assembly 210.

Figure 3A:
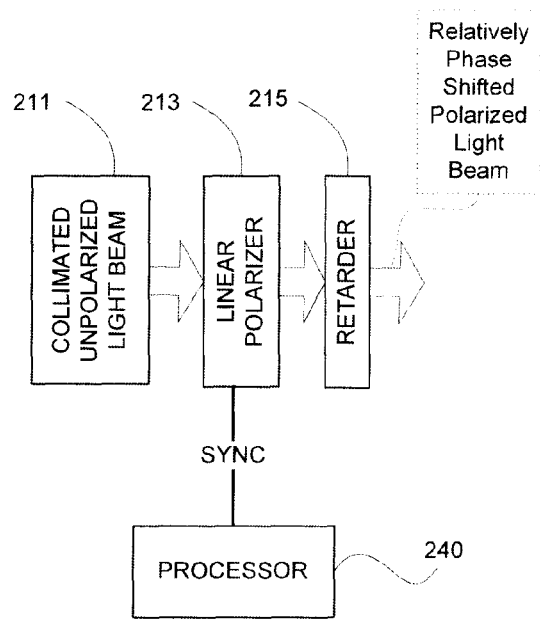
FIG. 3A illustrates synchronization of a processor to a rotatable linear polarizer.

FIG. 3A shows the synchronization line linked from the processor 240 to linear polarizer 211 such that for every image captured, the relative orientation of the linear polarizer 211 is known. The initial orientation of the linear polarizer does not need to be a particular fixed number. However, as the linear polarizer is rotated, that polarization orientation is made known to the processor 240.

Figure 3B:
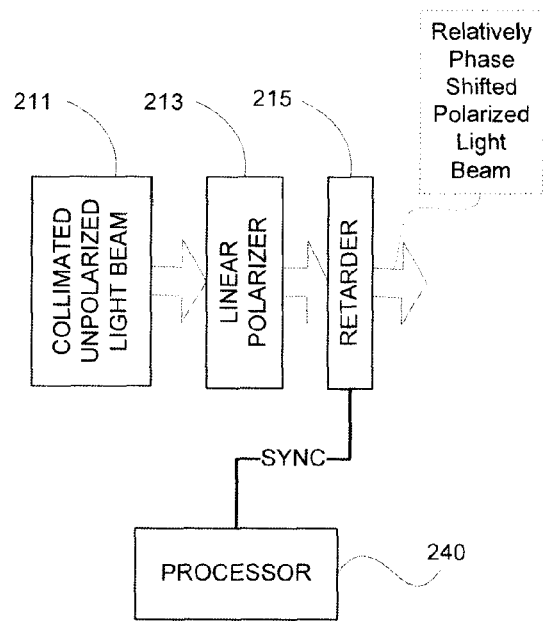
FIG. 3B illustrates synchronization of a processor to a rotatable or variable retarder.

In a slightly different setup, as shown in FIG. 3B, the synchronization line can be linked to control the orientation of a retarder 215 which delays the phase of one of the two orthogonal light polarizations by a selected value, usually expressed in terms of fractions of a wavelength. Typically, the retarder is a quarter wavelength retarder (called a quarter waveplate), which delays the phase of one polarization by a quarter wavelength (or 90°). If the two orthogonal polarizations have equal amplitude, the quarter waveplate retarder will produce light with a circular polarization. By rotating the retarder 251, the relative phase delay of the entire light beam is offset by the degree of rotation times two. The retarder 215 may also be a variable retarder (such as a Liquid Crystal Variable Retarder (LCVR)) to provide a selectable phase difference between the two orthogonal polarizations. When a variable retarder is used, no rotation of any assemblies is needed. Typically, an LCVR is controlled by a voltage applied to the LCVR, which adjusts the retardation on the slow axis of the LCVR. The selected phase differences through each cycle of retardation are controlled as phase settings of the retarder. The phase settings can be programmed into the processor to automate the retarder setting changes by commands from the processor to the retarder.

The birefringence of the substrate may be modeled as relative phase delay between two orthogonal polarization light beams. The measured intensity emerges from the product of a series of Jones matrix operating on the electric field of the linearly polarized light as shown in Eq. 1 below:

$$I = |J_{analyzer} \cdot J_{birefrigence} \cdot J_{sample} \cdot J_{birefrigence} \cdot J_{retarder} \cdot E_{linear\ polarizer}|^2 \quad \text{Eq. 1}$$

where $$E_{linear\ polarizer} = \begin{bmatrix} \cos[p] \\ \sin[p] \end{bmatrix}$$

and p is the orientation of the linear polarizer.

The Jones matrices for the other components of Eq. 1 are shown in Eqs. 2-5 below. Eq. 2 shows the Jones matrix for the retarder:

$$J_{retarder} = \text{Exp}\left(-i \cdot \frac{d}{2}\right) \quad \text{Eq. 2}$$

$$\begin{bmatrix} \cos\left(\frac{d}{2}\right) + i \cdot \sin\left(\frac{d}{2}\right)\cos(2r) & i \cdot \sin\left(\frac{d}{2}\right)\sin(2r) \\ i \cdot \sin\left(\frac{d}{2}\right)\sin(2r) & \cos\left(\frac{d}{2}\right) + i \cdot \sin\left(\frac{d}{2}\right)\cos(2r) \end{bmatrix}$$

where d is the retardation and r is the orientation of the retarder (either a quarter wave plate or LCVR).

Eq. 3 shows the Jones matrix for the specimen:

$$J_{sample} = \begin{bmatrix} 1 & 0 \\ 0 & \text{Exp}(i \cdot \delta_{sample}) \end{bmatrix} \quad \text{Eq. 3}$$

where $\delta_{specimen}$ is the amount of phase shift introduced by the specimen at the specimen to substrate interface.

Eq. 4 shows the Jones matrix for light transmission through the birefringent substrate:

$$J_{birefrigence} = \begin{bmatrix} \cos(b) & \sin(b) \\ -\sin(b) & \cos(b) \end{bmatrix} \begin{bmatrix} 1 & 0 \\ 0 & \text{Exp}(i \cdot \delta_{birefrigence}) \end{bmatrix} \quad \text{Eq. 4}$$

$$\begin{bmatrix} \cos(b) & -\sin(b) \\ \sin(b) & \cos(b) \end{bmatrix}$$

where $\delta_{birefringence}$ is the amount of phase shift introduced by the birefringence in the substrate, and b is the orientation of the birefringence. For simplification, b is assumed to be 0 for the following derivations. This implies that the direction of the molecules in the birefringent material are either parallel or perpendicular to the specimen plane, which is realistic for most substrates. This term operates on the electric field twice, once when the light enters the substrate and once when it exits the substrate. Eq. 5 shows the Jones matrix for the analyzer:

$$J_{analyzer} = \begin{bmatrix} \cos(a)^2 & \cos(a)\sin(a) \\ \cos(a)\sin(a) & \sin(a)^2 \end{bmatrix} \quad \text{Eq. 5}$$

where a denotes the orientation of the analyzer.

As shown by Eqs. 2 through 5, the full expansion of the final intensity value depends on the orientations of the different components in the optical path. However, the final intensity I can be simplified if some of the orientational parameters are assumed to have certain constant values. For example, if the orientations of the analyzer, a, and the linear polarizer, p, are chosen as 0.25π and the orientation of the retarder, r, is chosen as 0π, the intensity may be described as shown below in Eq. 6:

$$I = \cos\left(\frac{d + \delta_{sample}}{2} + \delta_{birefrigence}\right)^2 \quad \text{Eq. 6}$$

Birefringence can decrease or increase the intensity changes that would result just from a phase shift (i.e., polarization change) due to the specimen. It depends on which part of the cosine curve the phase shift of the specimen is at. For example, if the specimen phase shift is a small change around a multiple of 2π (where 2π is a polarization null), birefringence would offset the function from the insensitive plateaus and, in fact, increase the sensitivity of intensity to the phase shift due to the specimen.

In Eq. 6, the intensity is shown to be a function of variable retardation, since d is the variable retardation value. In other embodiments, the linear polarizer or retarder orientation may be variable, while the other components are fixed. In all three scenarios discussed above, the orientations of the linear polarizer 213, retarder 215, and the analyzer 231 are important. Table 1 describes required orientations of these components, relative to 0°, where 0° is pointing up perpendicularly into the specimen 223. The orientations are absolute angular differences from 0°. The direction of the difference, which would result in a constant offset of the measured value, does not matter.

TABLE 1

| Method | Polarizer Angle | Retarder Angle | Analyzer Angle | Retardation |
|---|---|---|---|---|
| Rotating Polarizer | variable | 0° or 90° | ±45° | ±90° |
| Rotating Retarder | ±45° | variable | ±45° | ±90° |

TABLE 1-continued

| Method | Polarizer Angle | Retarder Angle | Analyzer Angle | Retardation |
|---|---|---|---|---|
| Variable Retardation | ±45° | ±0° or 90° | ±45° | Variable |
| Rotating Analyzer | ±45° | 0° or 90° | variable | ±180° |

The intensities as a function of the controlled variable are described in the equations set forth below. The intensity at each pixel of the two dimensional detector 233 may be different during a single measurement, because the phase changes due to the birefringent substrate may be spatially changed. Eq. 7 below shows the intensity obtained with the variable retardation method described above. Note that the intensity is a function of the condition of the specimen, the birefringence of the substrate, and the controlled variable retardation.

$$I(\text{phase}_{retardation}) = \cos\left(\frac{\text{phase}_{sample} + \text{phase}_{retardation}}{2} + \text{phase}_{birefringence}\right)^2 \quad \text{Eq. 7}$$

Eq. 8 below shows the intensity obtained with the rotating polarizer method.

$$I(\text{polarizer orientation}) = \cos\left(\text{phase}_{rotation} - \frac{\text{phase}_{sample}}{2} - \text{phase}_{birefringence}\right)^2 \quad \text{Eq. 8}$$

Eq. 9 below shows the intensity obtained with the rotating retarder method where the retarder is a half-wave plate.

$$I(\text{retarder orientation}) = \quad \text{Eq. 9}$$
$$\frac{1}{2}(1 - \cos(\text{phase}_{sample} + 2 \times \text{phase}_{birefringence}))$$
$$(2\cos(2 \times \text{phase}_{orientation})^2 - 1))$$

Eq. 10 below shows the intensity obtained if the analyzer is rotated.

$$I(\text{analyzer orientation}) = \quad \text{Eq. 10}$$
$$\frac{1}{2}(1 - \cos(\text{phase}_{sample} + 2 \times \text{phase}_{birefrigence}))$$
$$(2\cos(\text{phase}_{orientation})^2 - 1))$$

Polarization phase can be extracted from all pixels of the two dimensional imaging array by performing a Fourier transformation on as few as four images at each pixel. The images should be spaced evenly through a complete cycle of these periodic functions (the period is 180° for square of cosine functions). For example, if four images are taken using the variable retardation method, each image should be retarded by 90° from each other as indicated by Eq. 7 above. If the rotated polarizer or analyzer method is used, the polarizer should be rotated 45° in each image as indicated by Eqs. 8 or 10 above. If the rotated retarder method is used, the retarder should be rotated by 22.5° from image to image as indicated by Eq. 9 above.

The phase change, as one value, is extracted from the images by performing a Fourier transform, in a manner similar to the Fourier transform ellipsometry described above. If four images are taken, then at a given imaging location, the four intensity values are fed into the Fourier transform which generates two numbers, amplitude and phase. When the Fourier transform is applied on every single pixel, an image of amplitude values and an image of phase values would be generated. The phase value of the specimen can be extracted by performing the Fourier transform ellipsometry before the specimen is added, so that the result obtained contain only the birefringence phase impact. This is termed a baseline measurement. The specimen is then added and the Fourier transform ellipsometry is performed again using multiple images. Simple subtraction is then used to remove the impact of birefringence from the measured signal.

Eq. 11 and 12 below show how Fourier transformation is performed with data obtained from the use of a variable retarder. Eq. 7 to 10 can be expanded and expressed as terms that contain the controlled variable, which can be the orientation of a component or the retardation value, and terms that are not directly controllable. The Fourier method extracts the exact phase shift from the terms containing the controllable variables, denoted as $\delta$ in Eq. 11. The Fourier transformation of the not-directly controllable terms yields zero. The change in specimen phase shift, $\delta_0$, over time can be viewed as a change from the baseline which includes the birefringence. In a continuous mathematical model, intensity images as functions of $\delta$ undergo the Fourier Transformation as shown below:

$$X = \int_0^{2\pi} \cos\left(\frac{\delta + \delta_0}{2}\right)^2 \cos(\delta) d\delta = \frac{\pi}{2}\cos(\delta_0) \quad \text{Eq. 11}$$

$$Y = \int_0^{2\pi} \left(\frac{\delta + \delta_0}{2}\right)^2 \sin(\delta) d\delta = \frac{\pi}{2}\sin(\delta_0)$$

The exact phase shift can then be computed as shown in Eq. 12 below:

$$\delta_0 = \arctan\left(\frac{Y}{X}\right) \quad \text{Eq. 12}$$

In practice, the variable retardation values can be set to discrete values, such as 0, 0.5π, π and 1.5π to obtain a reasonable calculation for the exact phase shift. Eqs. 11 can be discretized as $$X = \sum_{i=0}^{n} \cos\left(i * \frac{360°}{n}\right) I_i \quad \text{Eq. 13}$$

$$Y = \sum_{i=0}^{n} \sin\left(i * \frac{360°}{n}\right) I_i$$

where n is the total number of measurements, i is the index of each measurement, and I is the intensity value measured. Note also that Eq. 11 is expressed in terms of varying the retardation. Similar equations can be derived when the orientations of the linear polarizer or retarder are varied.

In Eqs. 9 to 10, the square of cosines are modulated by the functions of the specimen variables: the phase of the specimen and the phase of the birefringence. The functional forms are cosine functions, similar to the phase part. When the specimen variables are in the format of Eqs. 9 to 10, that is, appearing as the modulation of the controlled variable, they can be extracted from the amplitude of the Fourier transform, as shown in Eqn. 14.

$$\text{Amplitude} = \sqrt{X^2 + Y^2} \qquad \text{Eq. 14}$$

It is also possible to mix the above modes and control more than two variables on the instrument at the same time. For example, when the phases of specimen and birefringence add up to exactly integer multiple of 360°, the amplitude of Eq. 8 becomes zero regardless of the orientation of the analyzer. The phase cannot be measured when there is no amplitude. In this case, rotating the retarder or changing the polarizer orientation by a fixed amount can move the amplitude away from the zero point.

Figure 4:
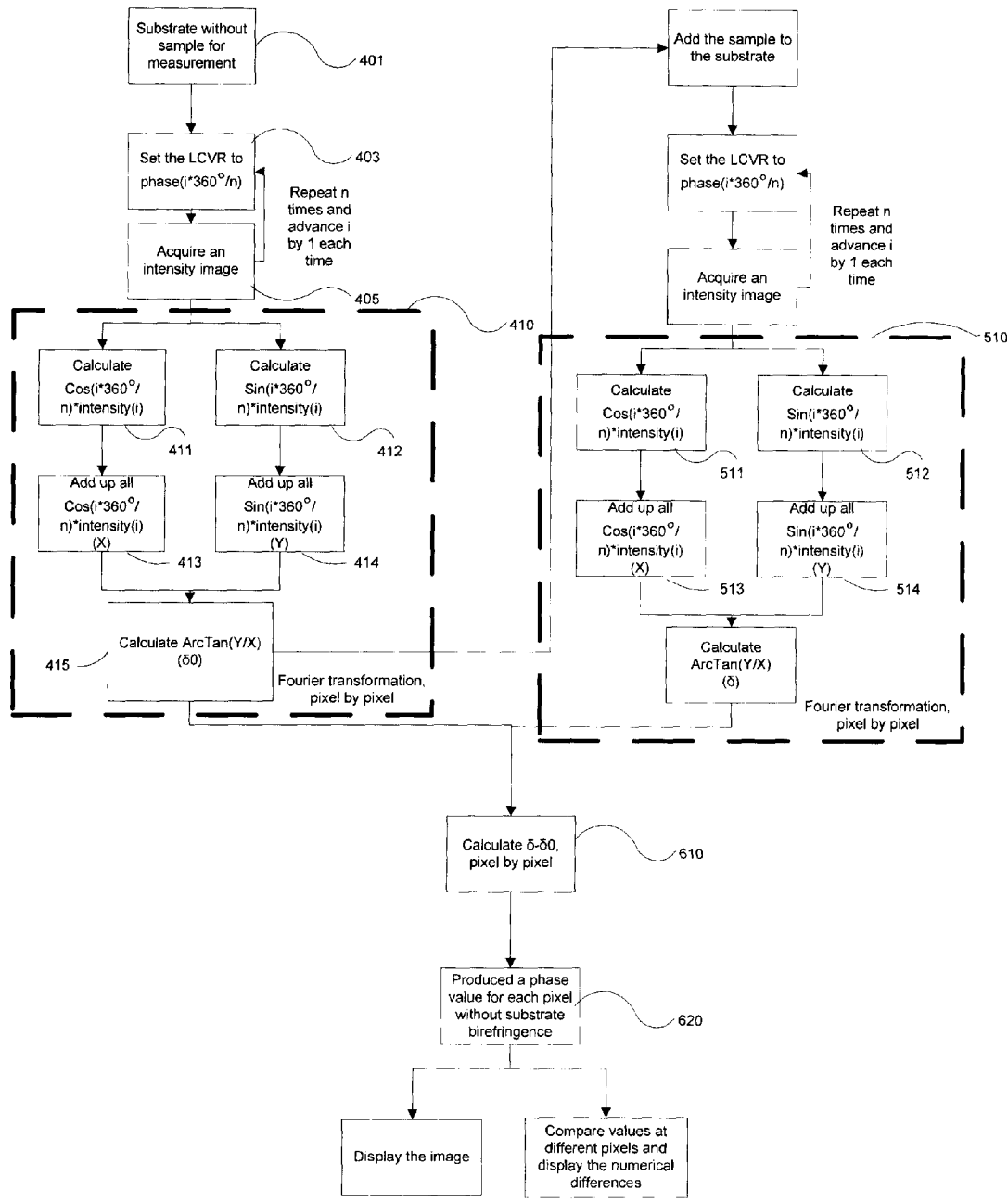
FIG. 4 illustrates data processing steps for generating a phase image that represents phase changes in a measured specimen.

FIG. 4 illustrates the data processing steps according to an embodiment of the present invention. The following explains how data is acquired and sent to a specially programmed computer which is programmed to perform the calculations in order to correct for birefringence caused by the substrate or slide on the surface of which the specimens have been deposited over a 2D area and thereby provide an image based only on the phase changes caused by the specimens in the evanescent field in which the 2D area is contained. In step 401, a substrate is positioned within a single reflection assembly (such as the assembly 220 shown in FIGS. 1 and 2). Polarized light is directed towards the substrate with the polarization set to a specified phase. Step 403 shows that a retarder such as an LCVR set to a phase i*360°/n, specified by the ith step of acquisition and the total number of n acquisitions. In the case where an LCVR is used, the computer is programmed to set the retarder to the selected phases and to record the phase settings. Other embodiments may use other devices or methods for selecting the phase of the polarized light as described above, but in each case the phase settings are saved in or inputted into the processor. Step 405 shows that a two-dimensional intensity image of the light reflected from the substrate is then acquired using a light detection device, such as a charge-coupled detector. The detector typically comprises hundreds to millions of detecting pixels arranged in a two-dimensional array. The term "intensity image" at 405 is intended to mean a set of intensity values for each pixel at each setting of the LCVR. An intensity value for each pixel is then provided to the computer or computer storage device, so the computer or computer storage device stores an intensity image which is an array containing hundreds to millions of intensity values for reflected light at the specified phase, that is, an intensity value for each pixel. As shown by steps 403 and 405, the LCVR is then set to another phase and another intensity image is acquired and stored. The steps of setting the LCVR and acquiring an intensity image are repeated four times at selected four different phases. While this description speaks of four phase settings, it is understood that more than four phase settings may be used. The phase settings are input to the computer which is programmed to use the settings to control the LCVR. The acquired image intensity data is sent to the computer and stored for use as below. Box 410 then shows that a Fourier transform is performed on the acquired and stored data. The Fourier Transform calculations may be performed by a specially programmed general purpose computer, signal processing hardware, programmable logic devices, or other processing and/or calculating devices which are specially programmed to perform the steps. Note that the Fourier transform is performed on a pixel-by-pixel basis. That is, a Fourier Transform is calculated using the intensity values at each different phase for a pixel to provide a Fourier Transform result for that pixel. The Fourier Transform calculations are performed for every pixel to provide a Fourier Transform result for every pixel in the intensity image. The steps within Box 410 show the calculations that may be used to perform the pixel-by-pixel Fourier Transform by the specially programmed computer. Step 411 shows a cosine calculation applied to the intensity values at a pixel and step 412 shows a sine calculation applied to the intensity values at the same pixel. The cosine results and sine results for the pixel are summed as shown in steps 413 and 414. The Fourier Transform result for the pixel is shown at step 415 by the arctangent calculation. Note again that these steps are performed for every pixel in the intensity image. The result of the calculations performed at step 415 is an array of values δ0.

The specimen testing portion of the procedure is then undertaken, again using the specially programmed computer to perform the following steps, generally the same as the steps with no specimen. Step 501 shows that a specimen is then positioned on the substrate. Similar to steps 403 and 405, steps 503 and 505 shows that retarder such as an LCVR is used to shift the phase of polarized light directed at the specimen, record the phase settings, and using intensity values for each phase setting, an intensity image is determined for each selected phase. The steps of shifting the phase of the polarized light and acquiring an intensity image are repeated at least four times at the selected four different phases and the intensity images at four different phases are acquired and stored. The four phases may be the same as or different than the phases used in steps 403 and 405. After the intensity images at several phases are acquired and stored, Box 510 shows that Fourier Transform calculations are performed by the specially programmed computer on a pixel-by-pixel basis for the intensity images acquired with a specimen on the substrate. Steps 511 and 512 show the performance of cosine and sine intensity calculations and steps 513 and 514 show the summation of those results. Step 515 shows a Fourier Transform result for each pixel is obtained by performing an arctangent calculation. The result from step 515 is an array of values δ. Step 610 shows that in the computer, the array of values δ0 is subtracted from the array of values δ to provide a resultant array of values where each value corresponds to a pixel in the two-dimensional detector. This resultant array may be displayed by a display device to show the detected specimen without distortions caused by birefringence in the substrate, as shown by step 620. The processing system may be configured to provide a user with simple intensity image or may apply other image manipulation techniques to highlight the polarization changes due to the specimen under evaluation. The processing system may also be configured to provide data to other processes or devices for further analysis of the data.

In all of the foregoing, and including variations in which the phase changes are accomplished by changing the settings of the polarizer, variable retardation and varying the analyzer, the rules set out in Table 1 above must be observed and the computer is programmed accordingly.

As discussed above, the phase change due to the non-birefringent free substrate contributes linearly to the phase change of the combination of the non-birefringent free substrate and the specimen(s). Thus, the phase change due to the non-birefringent free substrate can simply be subtracted from the phase change due to the combination of the non-birefringent free substrate and the specimen(s) to obtain the phase change resulting from the specimen(s) alone. Step 600 represents this subtraction, which is performed by subtracting each pixel of the substrate only phase image 420 from the corresponding pixel in the substrate/specimen(s) phase image 520. The resultant phase image 620 represents the phase or polarization shifts due to the specimen(s) alone.

Note that while the description above refers to operations being performed on pixels within the intensity images, these pixels may be grouped into locations for processing. That is, the intensity values for multiple pixels may be summed or summed and normalized to produce intensity values for locations within the two-dimensional detector before performing Fourier transforms on the location intensity values to reduce the number of Fourier calculations required. Fourier transform calculations techniques such as a Fast Fourier Transform calculation may also be used to speed the calculation of the Fourier Transform data.

Figure 5A:
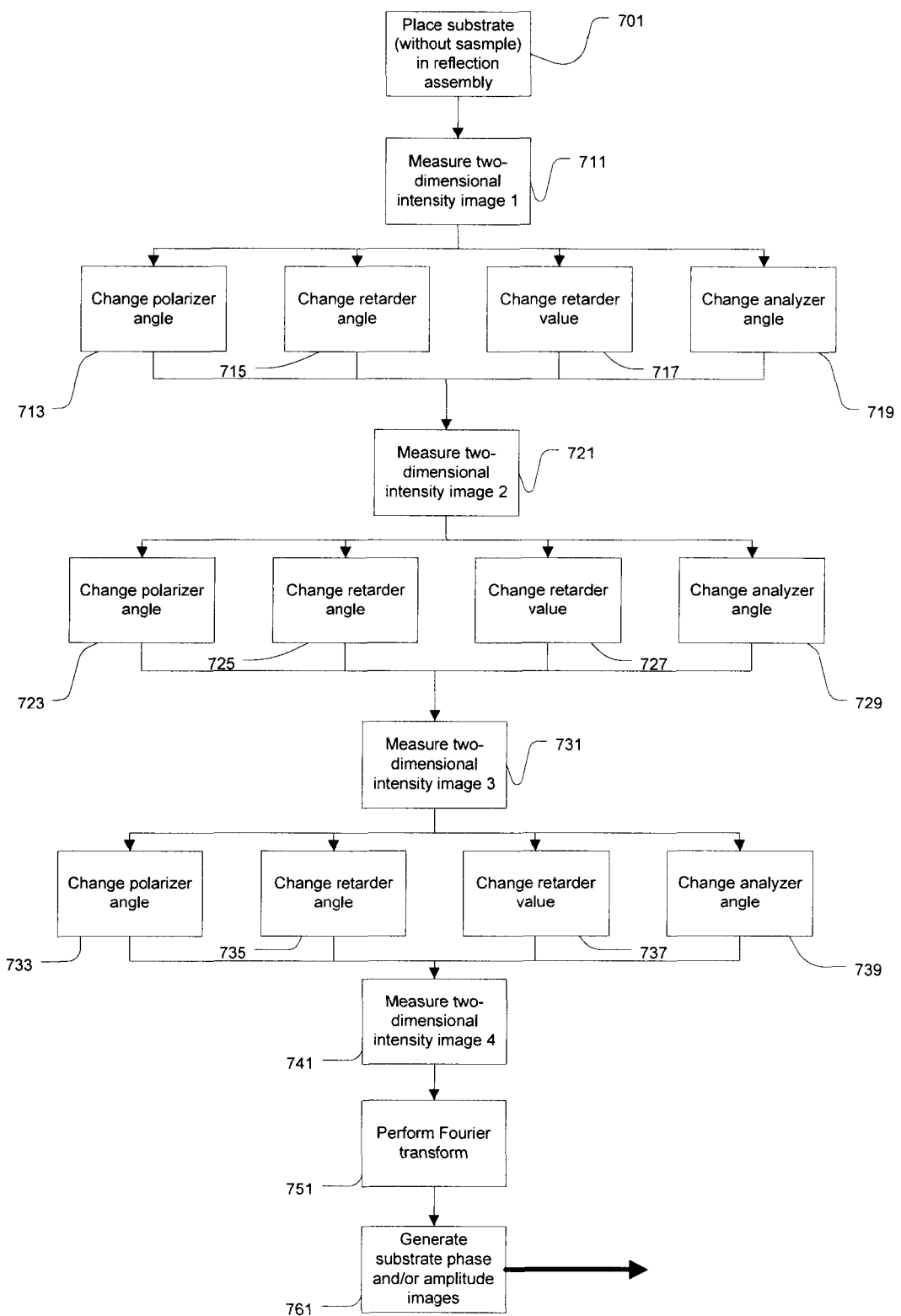
FIG. 5A shows the steps for measuring the phase changes due to a non-birefringent free substrate using the system depicted in FIG. 2.
Figure 5B:
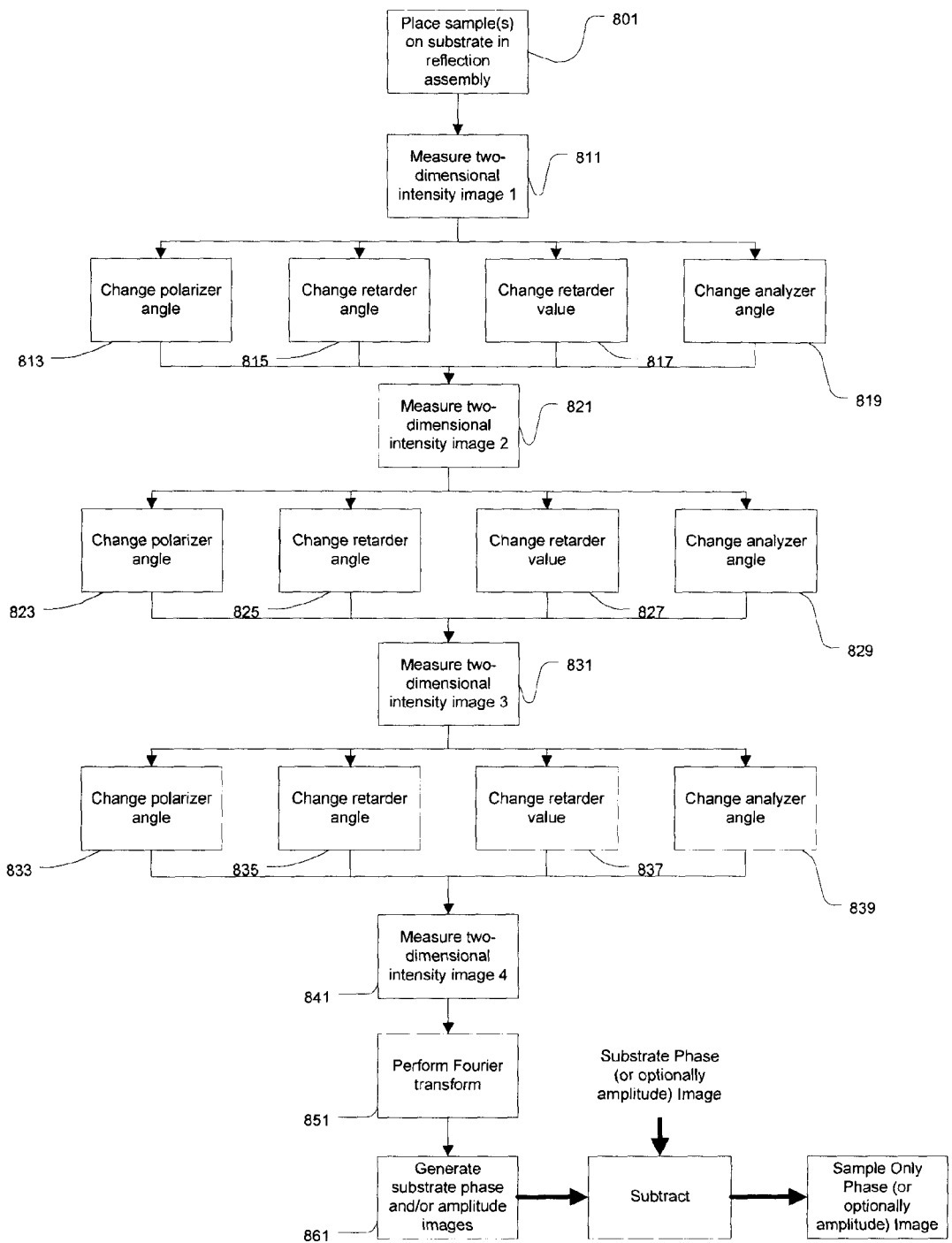
FIG. 5B shows the steps for measuring the phase changes in a substrate and specimen combination using the system depicted in FIG. 2 and obtaining a phase image that represents phase changes in a measured specimen.

FIGS. 5A and 5B show the steps to obtain the specimen only phase image using the system depicted in FIGS. 1 and 2. These steps are performed as above using the specially programmed computer/processor. In FIG. 5A, step 701 represents placing the non-birefringence substrate into the single reflection assembly 220 of FIG. 2. Step 711 represents the measurement of a first intensity image with the two-dimensional detector 233 at an initial phase angle. The phase of light is then changed by performing one or more of the following actions: changing the angle of the linear polarizer 213 as shown in step 713; changing the angle of the retarder 215 as shown in step 715, changing the value of the retarder 215 as shown by step 717, and changing the angle of the analyzer 231 as shown by step 719. Step 721 shows the measurement of a second intensity image at the second phase angle. The phase of light is then again changed by performing one or more of the following actions: changing the angle of the linear polarizer 213 as shown in step 723; changing the angle of the retarder 215 as shown in step 725, changing the value of the retarder 215 as shown by step 727, and changing the angle of the analyzer 231 as shown by step 729. Step 731 shows the measurement of a third intensity image at the third phase angle. The phase of light is then changed for a third time by performing one or more of the following actions: changing the angle of the linear polarizer 213 as shown in step 733; changing the angle of the retarder 215 as shown in step 735, changing the value of the retarder 215 as shown by step 737, and changing the angle of the analyzer 231 as shown by step 739. Step 741 shows the measurement of a fourth intensity image at the fourth phase angle. Step 751 represents the performance of a Fourier Transformation on the measured intensity images to generate an amplitude image and a phase image 761 for the substrate.

In FIG. 5B, step 801 represents placing a specimen or specimens on the non-birefringence substrate into the single reflection assembly 220 of FIG. 2. Step 811 represents the measurement of a first intensity image with the two-dimensional detector 233 at an initial phase angle. Note that this initial phase angle or the subsequent angles do not have to be the same as those used to measure the substrate only. The phase of light is then changed by performing one or more of the following actions: changing the angle of the linear polarizer 213 as shown in step 813; changing the angle of the retarder 215 as shown in step 815, changing the value of the retarder 215 as shown by step 817, and changing the angle of the analyzer 231 as shown by step 819. Step 821 shows the measurement of a second intensity image at the second phase angle. The phase of light is then again changed by performing one or more of the following actions: changing the angle of the linear polarizer 213 as shown in step 823; changing the angle of the retarder 215 as shown in step 825, changing the value of the retarder 215 as shown by step 827, and changing the angle of the analyzer 231 as shown by step 829. Step 831 shows the measurement of a third intensity image at the third phase angle. The phase of light is then changed for a third time by performing one or more of the following actions: changing the angle of the linear polarizer 213 as shown in step 833; changing the angle of the retarder 215 as shown in step 835, changing the value of the retarder 215 as shown by step 837, and changing the angle of the analyzer 231 as shown by step 839. Step 841 shows the measurement of a fourth intensity image at the fourth phase angle. Step 851 represents the performance of a Fourier Transformation on the measured intensity images to generate a phase image 861 for the specimen and substrate combination. Step 871 represents the subtraction of the substrate only image 761 from the specimen and substrate phase image 861 to generate a specimen only phase image 881.

The changes in the polarizer, retarder, or analyzer angle or the retardation value should follow the procedures described above. Also, as mentioned above, more than four different phases may be used to generate more than four intensity images for either substrate only images or specimen and substrate images. Also, as discussed above, the intensity images may be based only on pixel values or on values for groups of pixels. The phase images may be represented as two-dimensional matrices or with vectors or other data structures.

Figure 6:
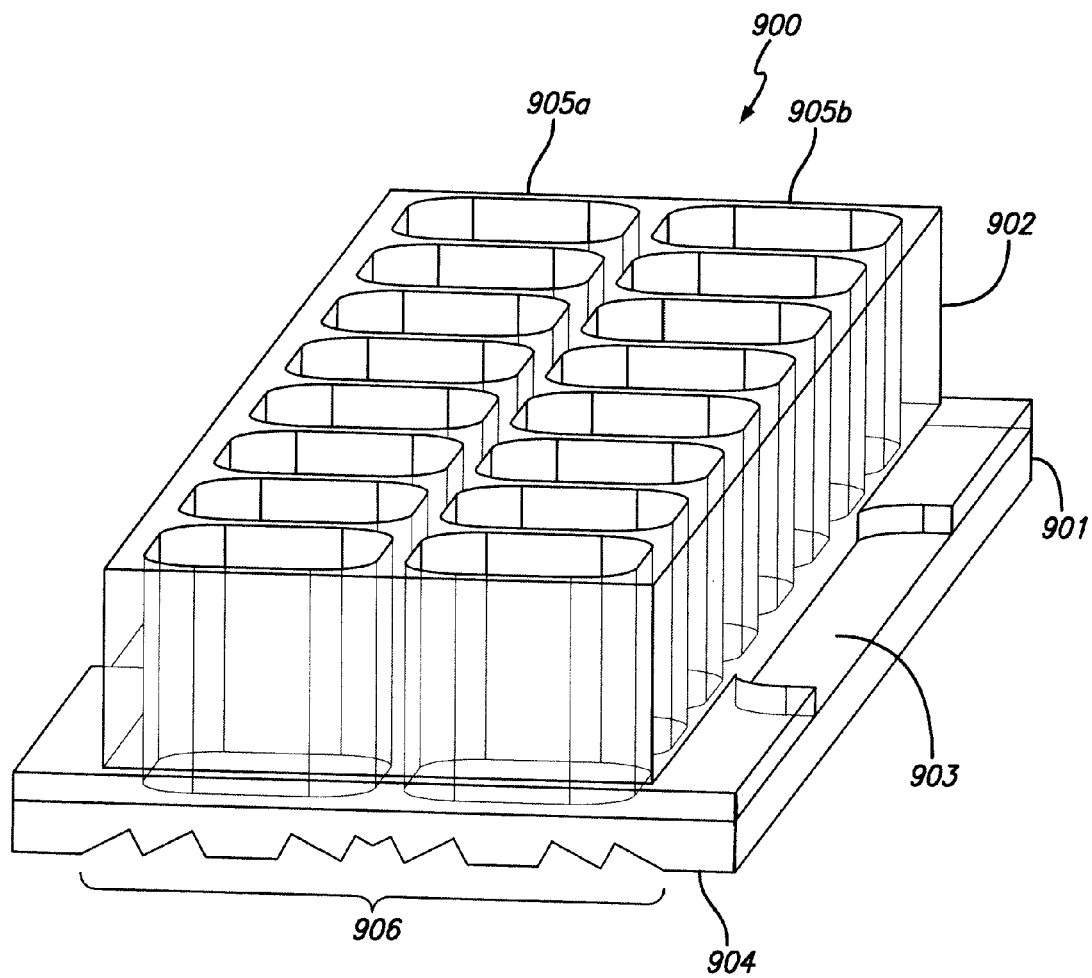
FIG. 6 depicts a front-top perspective view of an assembled slide with a multiwell plate attached.
Figure 7:
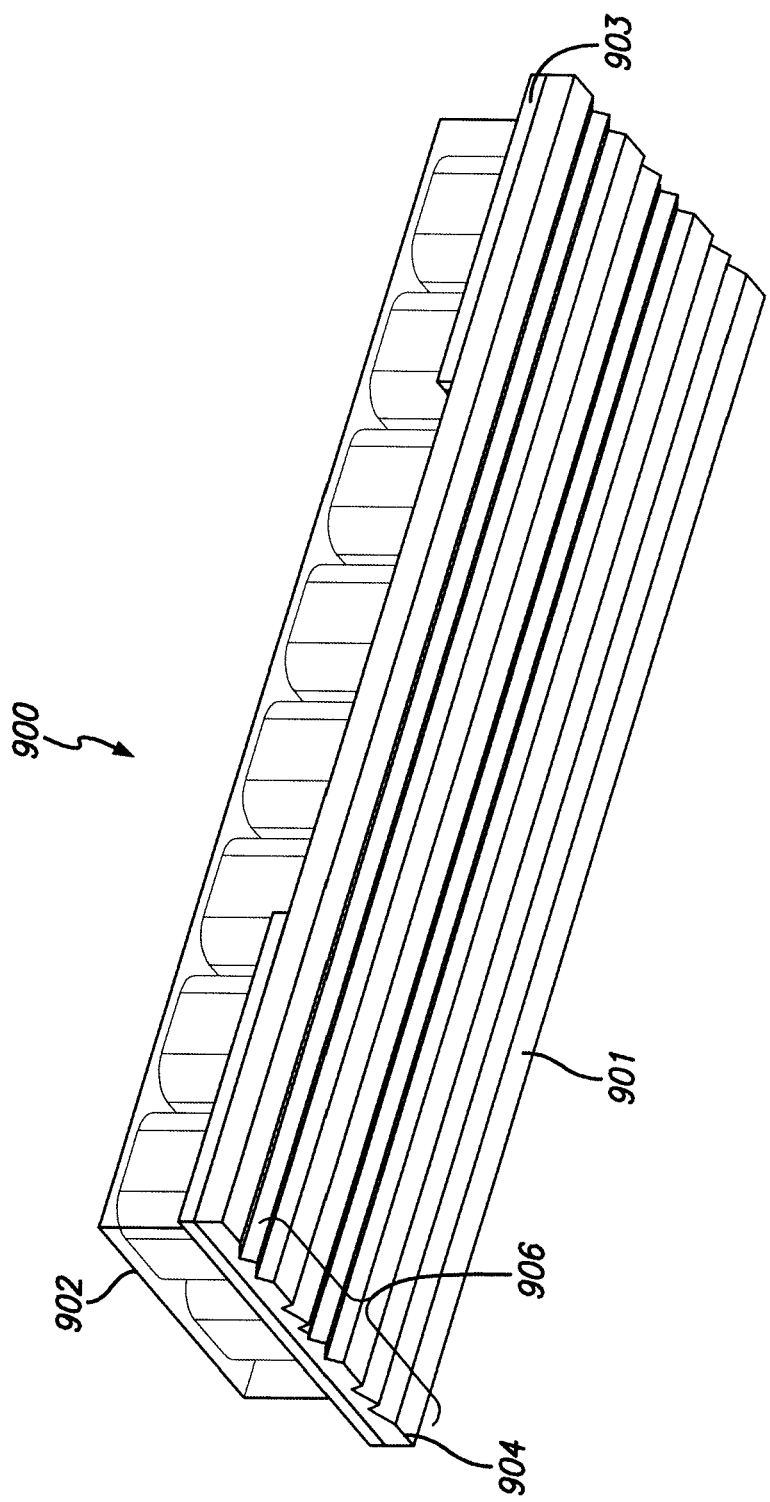
FIG. 7 depicts a front-bottom perspective view of the assembled slide and multiwell plate of FIG. 6.

Now referring to FIGS. 6 through 9. In FIGS. 6 and 7 there is shown a slide assembly 900 (see 220 at FIG. 2) having a slide, also referred to as a substrate 901 and a multiwell plate 902 which is securely mounted on the slide. The slide 901 has an upper surface 903 and a lower surface 904. The multiwell plate 902 is shown transparently and has two rows of wells 905a and 905b. Wells 905a and 905b are open at the bottom for access to the upper surface 903 of the substrate. The lower or bottom surface 904 of the substrate is configured with a set of grooves defining prismatic surfaces 906 extending the length of the substrate. Referring to FIG. 8, there is shown a light beam 907a aimed along axis 908a, at the bottom of the substrate 901. The beam hits the grooves which define two adjacent prismatic light incident surfaces 906a such that the beam passes into the substrate and reflects at the upper surface 903 then extending as an exiting beam of light 907b through and out of the substrate 901 along axis 908b passing across the grooves which define two prismatic light exiting surfaces 906b. The surfaces 906a and 906b are set at selected angles to control the direction of the beam in the substrate to establish an evanescent field at the surface 909, and in the example illustrated they are normal to the axis 908 of the incoming beam, although they could be at an angle to the beam axis. The area 909 is therefore where specimens can be studied by practice of the invention described herein. In the particular case of FIG. 8, the beam or the slide assembly, preferably the latter as shown by the arrow 910, will be moved so that the beam can be aimed at the second row of wells 905b. FIG. 9 shows a substrate (slide) 1004 that has a set of single grooves. The groove aligned with the incoming beam axis 1008a defines a prismatic light incident surface 1006a and the groove aligned with the exiting beam axis 1008b. Therefore, an evanescent field is at area 1009 at the surface 1003.

In all cases the angle of entry and exit of the beam must enable formation of an evanescent field. It is well known that at the "critical angle" under Snell's law an evanescent field is established. Total internal reflection (TIR), where the amount of light available for detection is maximized, is understood to be the preferred condition for selecting the angle. Angles at or more than the critical angle will result in total internal reflection. But total internal reflection is not required for functioning of this system and method herein. In practical application, the equipment may not allow an angle for total internal reflection, or it may not allow for precise setting. Angles less than the critical angle will work, with of course decreasing intensity of the reflected beam as the angles gets further away from the critical angle. Further because of variables in a particular set up, the critical angles may not be exactly known. It has been found that even as little as 10% of the light returning in the reflected beam can give useful results in some set-ups.

While the foregoing describes one type of biochip, they come in many forms and it is a rapidly evolving technology. In general it can be appreciated that biochips come to a user in two generic types. One type has the probes or other chemistry already deposited on a surface and the other type permits the user to deposit material onto the surface. The terms "microarray" and micro fluidic array" also define types of biochips. The present invention is understood to apply to any type of biochip that can be implemented for study of material on a surface by single internal reflection of polarized light to determine polarization phase shift caused by the material under study including comparison of phase shift for study of changes in the material that is imaged by sequential reflection measurements and imaging.

The foregoing Detailed Description of exemplary embodiments is presented for purposes of illustration and disclosure in accordance with the requirements of the law. It is not intended to be exhaustive nor to limit the invention to the precise form or forms described, but only to enable others skilled in the art to understand how the invention may be suited for a particular use or implementation. The possibility of modifications and variations will be apparent to practitioners skilled in the art.

No limitation is intended by the description of exemplary embodiments which may have included tolerances, feature dimensions, specific operating conditions, engineering specifications, or the like, and which may vary between implementations or with changes to the state of the art, and no limitation should be implied therefrom. In particular it is to be understood that the disclosures are not limited to particular compositions or biological systems, which can, of course, vary. This disclosure has been made with respect to the current state of the art, but also contemplates advancements and that adaptations in the future may take into consideration of those advancements, namely in accordance with the then current state of the art. It is intended that the scope of the invention be defined by the Claims as written and equivalents as applicable. It is also to be understood that the terminology used herein is for the purpose of describing particular embodiments only, and is not intended to be limiting. Reference to a claim element in the singular is not intended to mean "one and only one" unless explicitly so stated. As used in this specification and the appended claims, the singular forms "a," "an," and "the" include plural referents unless the content clearly dictates otherwise. The term "several" includes two or more referents unless the content clearly dictates otherwise. Unless defined otherwise, all technical and scientific terms used herein have the same meaning as commonly understood by one of ordinary skill in the art to which the disclosure pertains.

Moreover, no element, component, nor method or process step in this disclosure is intended to be dedicated to the public regardless of whether the element, component, or step is explicitly recited in the Claims. No claim element herein is to be construed under the provisions of 35 U.S.C. Sec. 112, sixth paragraph, unless the element is expressly recited using the phrase "means for . . . " and no method or process step herein is to be construed under those provisions unless the step, or steps, are expressly recited using the phrase "comprising step(s) for . . . ."

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A method for analyzing a specimen comprising:
providing a source of a directed polarized beam of light having a polarization and a two dimensional array of sensors defining an array of pixels;
directing the directed polarized beam of light as an incoming polarized beam of light at a transparent substrate, wherein the transparent substrate is configured to receive the specimen on a surface of the substrate and the incoming polarized beam of light is reflected by single internal reflection at the surface at a location where the specimen is to be positioned to establish a reflected polarized beam of light directed to the two dimensional array of pixels;
for each pixel of the two dimensional array;
   transforming the polarization of the directed polarized beam of light as received by each pixel to each of selected polarizations in a set of selected polarization orientations;
   measuring light intensity at each pixel at each of the selected polarization orientations;
   in a specially programmed computer Fourier transforming the measured light intensity of light at each pixel and calculating a baseline phase and baseline amplitude;
positioning a specimen on the transparent substrate;
directing a directed polarized beam of light as a second incoming polarized beam of light at the transparent substrate for single internal reflection at the surface on which the specimen is located to establish a second reflected polarized beam of light;
for each pixel;
   measuring light intensity in the second reflected beam of light from the specimen positioned on the substrate at each of the selected polarization orientations;
in the specially programmed computer Fourier transforming the measured light intensity specimen of the second reflected beam of light and calculating a specimen phase and specimen amplitude;
calculating a difference between the baseline phase and the specimen phase and optionally calculating a difference between the baseline amplitude and the specimen amplitude to obtain phase and optionally amplitude data for the specimen; and
using at least the phase data converting to image data for each pixel on a display connected to the computer; and
either or both, displaying on a display all or selected portions of the two dimensional area of sensors comprehended by the two dimensional array of sensors and
allowing use of the phase data and optionally of the amplitude data to compare portions of said data and to calculate the degree of changed effects of specimens over time.

2. The method according to claim 1, wherein transforming the polarization of the directed polarized light comprises rotating a linear polarizer.

3. The method according to claim 1, wherein rotating the polarization of the directed polarized light comprises rotating a retarder.

4. The method according to claim 1, wherein rotating the polarization of the directed polarized light comprises changing retardation of a variable retarder.

5. The method according to according to claim 1, wherein rotating the polarization of the directed light comprises rotating a polarization analyzer.

6. The method according to claim 1, wherein the Fourier transformation is comprised of $$X = \sum_{i=0}^{n} \cos\left(i * \frac{360°}{n}\right) I_i$$

$$Y = \sum_{i=0}^{n} \sin\left(i * \frac{360°}{n}\right) I_i$$

$$\text{phase} = \arctan(Y/X)$$

$$\text{Amplitude} = \sqrt{X^2 + Y^2}$$

where the i is the index of intensity measurement, n is the total number of measures, and I denotes the intensity reflected from the substrate and wherein baseline phase and specimen phase are equal to calculated phase and baseline amplitude and specimen amplitude are equal to calculated amplitude.

7. The method according to claim 1, wherein polarization orientations in the set of selected polarization orientations comprise evenly spaced angular offsets within a cycle of periodicity.

8. The method according to claim 1, wherein polarization orientations in the set of selected polarization orientations comprise four or more different angular offsets.

9. The method of claim 8 wherein the change in polarization orientations is done by changing the variable retarder and the processor is programmed for rotating the polarization of the directed polarized light commanding changing retardation of variable retarder.

10. The method of claim 9 wherein the polarized light source passes through a polarizer and the variable retarder, reflects from the substrate surface and then passes through an analyzer and then to the two dimensional array of sensors and the polarizer is set at 0 or 90 degrees and the analyzer is set at +45 degrees.

* * * * *